United States Patent [19]

Desnick et al.

[11] Patent Number: 5,449,865
[45] Date of Patent: Sep. 12, 1995

[54] EAR TIPS HAVING MOLDED-IN RECESSES FOR ATTACHMENT TO A STETHOSCOPE

[75] Inventors: Mandel L. Desnick, St. Louis Park; Brian J. Kompelien, Anoka, both of Minn.

[73] Assignee: Minnesota Mining and Manufacturing Company, St. Paul, Minn.

[21] Appl. No.: 187,851

[22] Filed: Jan. 28, 1994

[51] Int. Cl.6 .................................................. A61B 7/02
[52] U.S. Cl. .................................. 181/131; 181/135
[58] Field of Search .............. 181/130, 131, 135, 137; 381/67; 128/152, 864, 867

[56] References Cited

U.S. PATENT DOCUMENTS

| | | |
|---|---|---|
| 2,803,308 | 8/1957 | Di Mattia . |
| 2,888,921 | 6/1959 | Nielson et al. . |
| 3,108,652 | 10/1963 | Littmann . |
| 3,123,069 | 3/1964 | Laisne et al. . |
| 3,275,099 | 9/1966 | Speelman ................. 181/131 |
| 3,303,902 | 2/1967 | Knott . |
| 3,539,031 | 11/1970 | Scanlon . |
| 3,618,600 | 11/1971 | Douglas . |
| 3,710,888 | 1/1973 | Peart . |
| 3,732,382 | 5/1973 | DeWitt . |
| 3,768,470 | 10/1973 | Leight . |
| 3,881,570 | 5/1975 | Lewis . |
| 3,882,848 | 5/1975 | Klar et al. . |
| 3,895,627 | 7/1975 | Leight . |
| 3,896,801 | 7/1975 | Grout . |
| 3,935,401 | 1/1976 | Shore et al. . |
| 4,055,233 | 10/1977 | Huntress . |
| 4,261,432 | 4/1981 | Gunterman . |
| 4,434,794 | 3/1984 | Leight . |
| 4,443,668 | 4/1984 | Warren . |
| 4,540,063 | 9/1985 | Ochi et al. . |
| 4,564,009 | 1/1986 | Brinkhoff . |
| 4,607,720 | 8/1986 | Hardt . |
| 4,852,684 | 8/1989 | Packard . |
| 4,870,689 | 9/1989 | Weiss . |
| 4,913,259 | 4/1990 | Packard . |
| 4,969,534 | 11/1990 | Kolpe et al. . |
| 5,002,151 | 3/1991 | Oliveira et al. ................. 181/135 X |
| 5,044,463 | 9/1991 | Carr . |
| 5,046,580 | 9/1991 | Barton . |
| 5,074,375 | 12/1991 | Grozil . |
| 5,288,953 | 2/1994 | Peart ................. 181/131 X |

FOREIGN PATENT DOCUMENTS

| | | |
|---|---|---|
| 2310741 | 5/1975 | France . |
| 154516 | 7/1987 | Poland . |

OTHER PUBLICATIONS

Hal-Hen Company, Wholesale Net Price List, Long Island City, N.Y.

Littmann Classic II Stethoscope; 3M Health Care, 3M Center Bldg. 275-4E-01, St. Paul, Minn. 55144-1000; 70-2008-3506-7 (12.75)ii.

Littmann Master Classic Stethoscope; 3M Health Care, 3M Center Bldg. 275-4E-01, St. Paul, Minn. 55144-1000; 70-2008-4251-9 (12.75)ii.

3M Littmann Master Cardiology Stethoscope; 3M Health Care, 3M Center Bldg. 275-4E-01, St. Paul, Minn. 55144-1000; 70-2008-3508-3 (141.5)ii.

*Primary Examiner*—Howard B. Blankenship
*Assistant Examiner*—Khanh Dang
*Attorney, Agent, or Firm*—Gary L. Griswold; Walter N. Kirn; Jeffrey J. Hohenshell

[57] ABSTRACT

A stethoscope having a binaural with dual sound-transmitting tubes adapted to deliver sound to a human ear, with each tube having an ear tip connection end having a plurality of flanges thereon. Removably attached to the described tubes are a pair of ear tips formed of a non-porous elastomeric material having a channel therein having a plurality of molded-in recesses adapted to engage the flanges in complementary fashion.

20 Claims, 3 Drawing Sheets

EAR TIPS HAVING MOLDED-IN RECESSES FOR ATTACHMENT TO A STETHOSCOPE

TECHNICAL FIELD

This invention relates to ear tips to adapt stethoscopes to the human ear, and more particularly to features to improve the attachment of the ear tip to the stethoscope.

BACKGROUND

The stethoscope has long been an important part of medical diagnostics. Examples of such diagnostic stethoscopes are disclosed in U.S. Pat. Nos. 4,440,258; Des. 277,890; 4,475,619 and 4,995,473 the entire contents of each of which are herein incorporated by reference.

An important element of the stethoscope from the user's point of view is the ear tips as they determine much of how comfortable the instrument will be perceived in use. It is also known that a good acoustic seal between the ear tip and the ear is of great importance. Small leaks to the atmosphere or sound blockages in that location may cause attenuation of the sound energy or sound quality that is ultimately delivered to the ear.

Drawing lesser attention perhaps, but also important is that such ear tips should be capable of being removed for cleaning. Once cleaned, the ear tips may be replaced on the ends of the eartubes. Many cycles of such removal and replacement should be withstood by ear tips, since wax secretions are detrimental to many elastomers, and since buildup at the ear tip my cause blockage of the sound path. Also, such buildup may provide a vector for spreading infection.

Coassigned U.S. Pat. Nos. 4,913,259 and 4,852,684 (both to Packard et al. and which are herein incorporated by reference) disclose a compressible ear tip and its use on a stethoscope. It shows a non-porous elastomeric ear tip having a shoulder. Commercial embodiments of the ear tips shown in these patents have been sold more than one year prior to the filing date of the present application by Minnesota Mining and Manufacturing Co. (3M) of St. Paul, Minn. for use with the 3M Littman ™ Master Cardiology and the 3M Littmann ™ Cardiology II stethoscopes.

SUMMARY OF THE INVENTION

The present invention addresses the above identified limitations in the art of ear tips by providing a stethoscope having a binaural with dual sound-transmitting tubes for delivering sound to a human ear, with each tube having an ear tip connection end having a plurality of flanges thereon. Removably attached to the described tubes are a pair of ear tips formed of a non-porous elastomeric material having a channel therein having a plurality of molded-in recesses adapted to engage the flanges in complementary fashion.

Alternatively, the invention comprises the ear tip itself. The ear tip cooperates with a stethoscope having sound-transmitting eartubes for delivering sound to a human ear. Each eartube has an ear tip connection end having a plurality of flanges thereon. The ear tip has a body formed of a non-porous elastomeric material having a channel therein having plurality of molded-in recesses adapted to engage the flanges in complementary fashion. A feature of the invention is a complementary set of flanges on the eartubes and recesses in the ear tip which engage each other.

The present invention provides an ear tip for use with a stethoscope which: a) may be conveniently and repeatedly attached to and removed from the sound-transmitting tubes of a stethoscope, b) remains firmly attached to the sound transmitting tubes of a stethoscope, while having excellent maintenance of that attachment over repeated cycles of application and removal of the ear tip from the sound transmitting tubes, and c) optionally affords use with a threaded insert that enables the ear tip to be threaded onto a stethoscope with threaded sound transmitting tubes.

A further advantage of the invention is that the flanges on the eartube of the stethoscope can be fabricated by cutting relief into the outside diameter of simple tube stock by machining, thereby reducing production costs and material usage.

BRIEF DESCRIPTION OF THE DRAWINGS

A more complete understanding of the invention and its advantages will be apparent from the Detailed Description taken in conjunction with the accompanying Drawings, in which.

DETAILED DESCRIPTION

Figure 1:
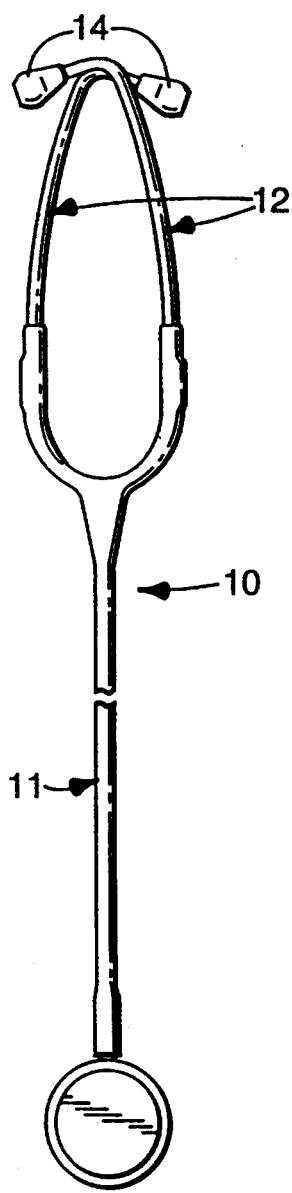
FIG. 1 is a plan view of a stethoscope according to the present invention.
Figure 2:
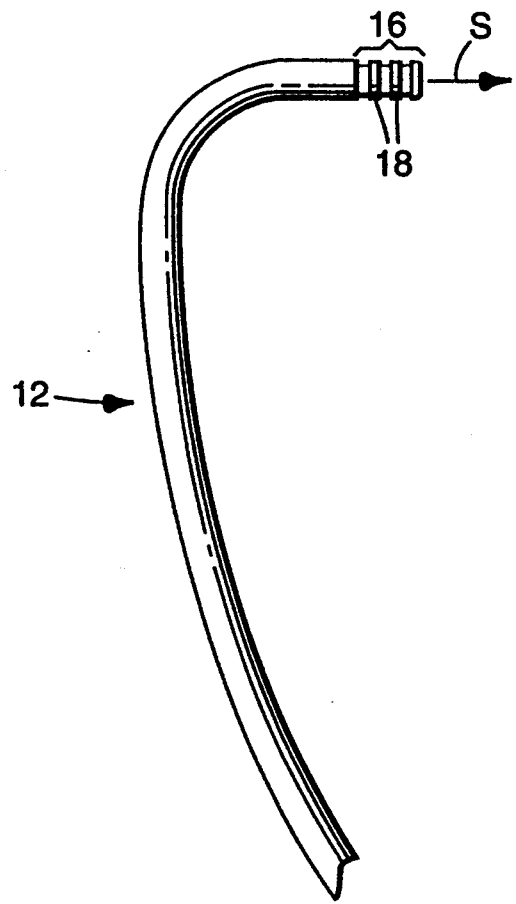
FIG. 2 is a detail plan view of a portion of one of the eartubes of the stethoscope of FIG. 1, with its ear tip removed.

Referring to FIG. 1, a side view of a spring-loaded stethoscope 10 is shown. The stethoscope has a binaural 11 with dual sound transmitting tubes 12 terminating in ear tips 14. In FIG. 2, a detail plan view of one of the sound transmitting tubes 12 of the stethoscope 10 of FIG. 1 is illustrated with its ear tip 14 removed for clarity. The ear tip connection end 16 of the sound transmitting tube 12 is shown in detail in FIG. 3. Here it will be seen that the ear tip connection end 16 has a plurality of flanges 18, and an ear tip connection end axis S (FIG. 2).

Figure 3:
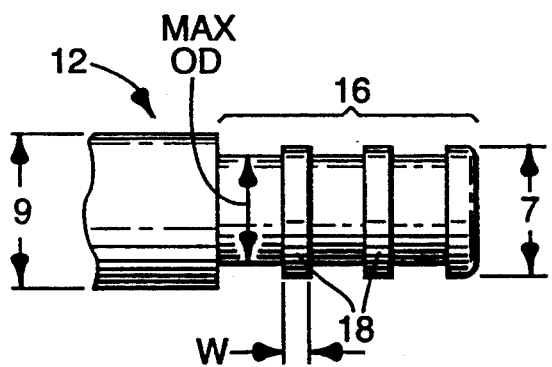
FIG. 3 is a detail plan view of the end of the eartube of FIG. 2.

The sound transmitting tubes 12 may be fabricated from any suitable materials, with hardened aluminum or stainless steel being considered particularly preferred. However, a suitable plastic material may optionally be used. The sound transmitting tubes 12 have a maximum outer diameter 9 (FIG. 3) and the flanges define a maximum flange diameter 7 (FIG. 3). Preferably, the maximum outer diameter of the sound transmitting tubes 12 is greater than or equal to the maximum flange diameter 7 so that the flanges 18 may be formed by machining the material used to construct the tubes 12 without necessitating the addition of material.

Figure 4:
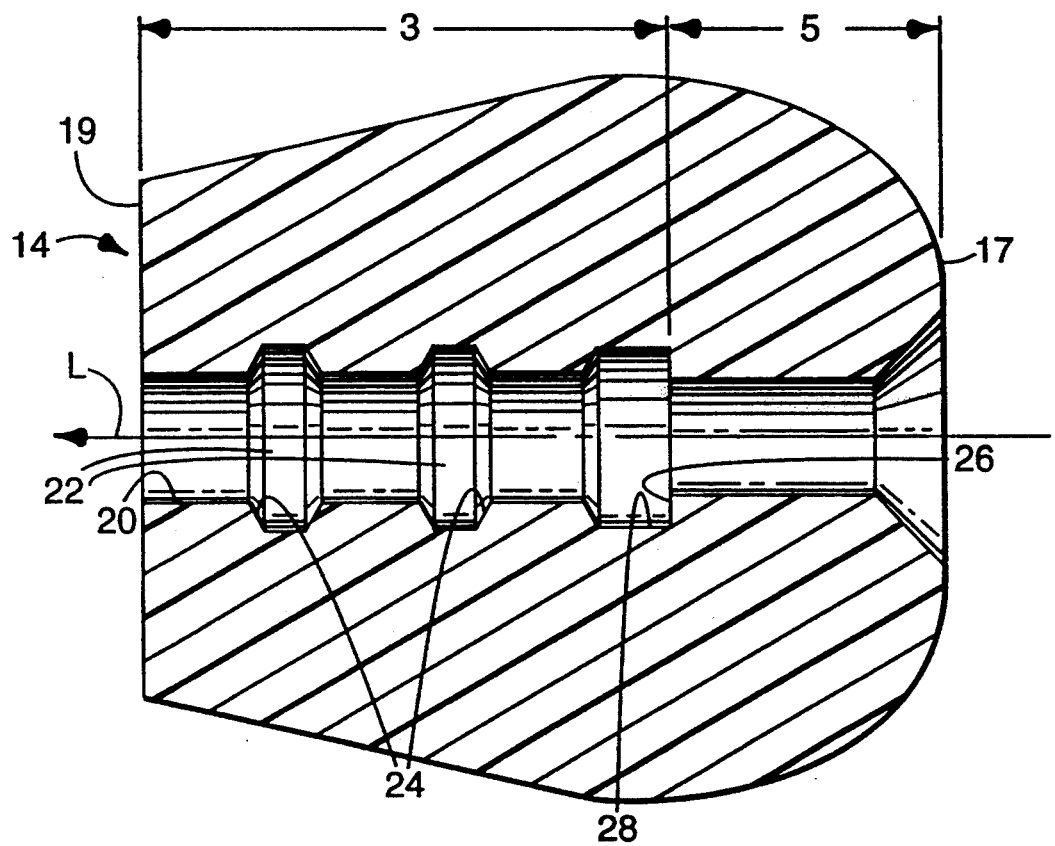
FIG. 4 is a cross section view of a first embodiment of ear tip according to the present invention.

An ear tip 14 according to the present invention is shown in FIG. 4 in cross section view. The ear tip 14 may generally be described as having an attachment section 3 and a generally arcuate ear engagement section 5 defining an ear engagement end 17 and an opposite end 19. Preferably, the attachment section is less than about 0.5 inches in length (more preferably less than about 0.4 inches) to avoid an overly lengthy ear tip and to afford efficient use of the materials used to construct the ear tip.

In the attachment section 3, the ear tip 14 has a central channel 20 for connection to the stethoscope 10 via ear tip engagement section 16 of the sound transmitting tube. Axially spaced within the channel 20 are a plurality of molded-in recesses 22. The channel 20 defines a longitudinal axis L for the ear tip 14.

Sides 24 of the recesses 22 are tapered in preferred embodiments to allow easy insertion and removal of the sound transmitting tubes 12 on the ear tip, and to avoid stress concentrations in the structure of the ear tip. The axially innermost side 26 of the innermost recess 28 is preferably square relative to the axis of the channel 20 to, among other things, prevent the inadvertent protrusion of the sound transmitting tube 12 into the ear of the user. When the ear tip is inserted on the stethoscope 10, all of the molded—in recesses 22 cooperably engage the flanges 18 on sound transmitting tubes 12 in complementary fashion such that the plurality of flanges resist longitudinal removal or movement of the ear tip 14 from the stethoscope.

Figure 5:
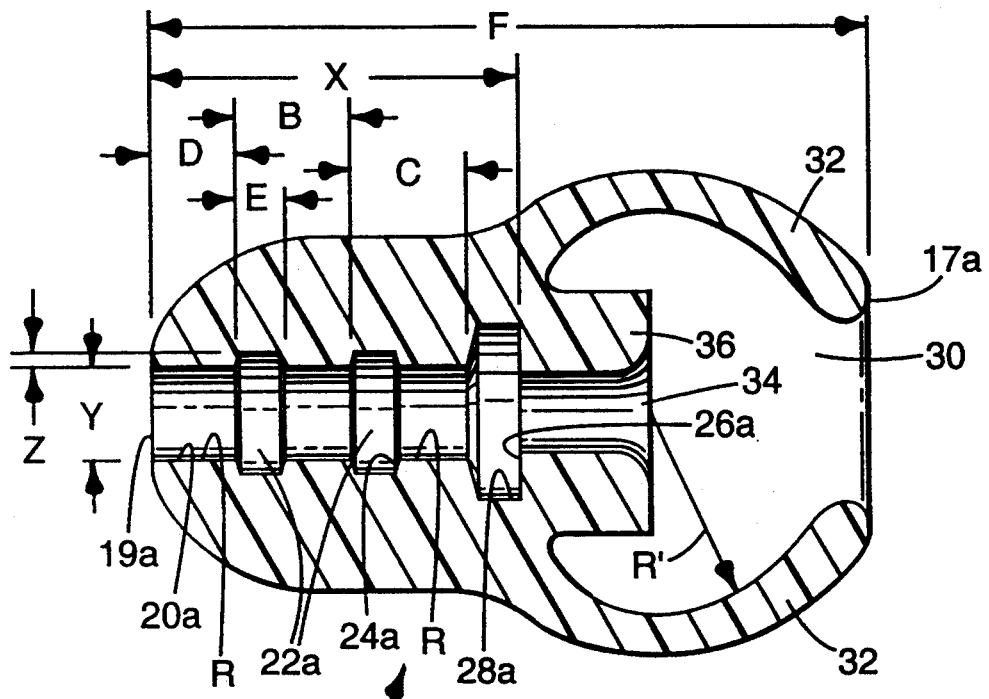
FIG. 5 is a cross section view of an alternate embodiment of an ear tip according to the present invention which illustrates a hollow ear tip connection section.

Referring now to FIG. 5, a cross section view of an alternate embodiment of an ear tip 14a is illustrated which has many of the features of the ear tip 14 which are identified by the same reference figure to which the suffix "a" has been added. The ear tip 14a has a hollow inner chamber 30 at its ear engagement end 17a defined by walls 32. Chamber 30 includes an entry port 34 defined by a short cylindrical stop 36 which projects into chamber 30 a predetermined distance to provide a stop means to prevent extensive inward compression of walls 32. Suitable construction details for this alternate embodiment (except for the mechanics of its attachment to the stethoscope's sound transmitting tubes) are discussed in U.S. Pat. No. 4,913,259 which is herein expressly incorporated by reference.

The ear tip 14a is preferably formed of a flexible, resilient material such as a non-porous elastomeric material. It is important that the ear tips of the present inventions be constructed of a material which is compatible with contact with the human ear. Suitable materials include vulcanized natural rubber, vinyl elastomers, elastomeric polyurethanes such as sold under the tradename REN:C:O-THANE by Ren Plastics Corp., silicone rubbers such as that sold under the designation "1940-50" by Shinetsu, nitrile rubbers, and thermoplastic rubbers, such as are sold under the tradename "Kraton G" by the Shell Chemical Company of Houston, Tex. Other suitable materials from which an ear tip may be fabricated include nitrile rubbers, and thermoplastic rubbers. Compatibility in this sense includes both resistance to the acidic oils present in the ear as well as low cytotoxicity. Optionally, an ear tip may be subjected to a surface treatment to provide a low coefficient of friction and anti-static properties.

An appropriate hardness is also important for providing comfort to the user of the stethoscope. Preferably, the hardness of the ear tip 14a should be between about 30 and 80 Shore A, and more preferably between about 40 and 70 Shore A. Most preferably, the hardness should be about 45 Shore A.

The number of flanges 18 on a sound transmitting tube 12 equals the number of recesses 24a in an ear tip 14a so that the ear tip 14a complements the stethoscope 12. As used herein, when it is said that a channel of an ear tip has a "plurality of molded-in recesses adapted to cooperably engage the flanges in complementary fashion such that the plurality of flanges resist longitudinal removal of the ear tip from the stethoscope", it is meant that, when the ear tip is fully inserted on the stethoscope, at least two of flanges (preferably three) physically interfere with or act as a barrier to longitudinal (axial) removal of the ear tip from the stethoscope, as opposed to, for example a mere radial interference fit between the ear tip and stethoscope.

Between the recesses 22a, the sides 24a form the sides of ear tip ribs R. The sides 24a of the two recesses 22a closest to the end 19a are situated at an acute, included angle relative to the base of the rib R. If the base of the rib R is generally parallel to the longitudinal axis L, then the acute, included angle is preferably approximately seventy-five degrees. For a rib with sides at approximately a seventy-five degree angle with respect to its base, the width and height of the rib are preferably within the following parameters:

$$0.3\ J > N > 20\ J$$

wherein:

N = width of the base of the rib R, and

J = height of the rib R.

Structure meeting this equation provides for a rib with a slender tip which is readily deflected to afford convenient insertion and removal of the ear tip, and a relatively wide base which resists removal or axial movement of the ear tip from the stethoscope and damage even after repeated uses. If the base of the rib R becomes too wide relative to the height, then the rib tends to become unduly stiff which adversely increases the insertion and removal forces for the ear tip. If the base of the rib R becomes too small relative to the height, then the rib tends to become too flexible which adversely reduces the removal force characteristic of the ear tip.

Figure 6:
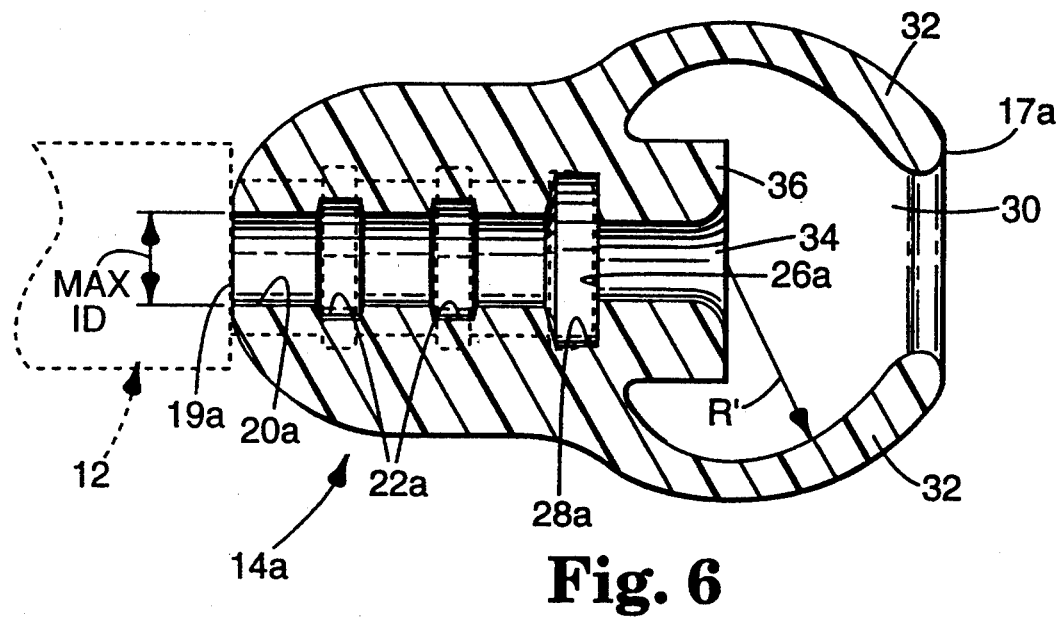
FIG. 6 is a schematic illustration of the distal end portion of the stethoscope and sectional illustration of the ear tip according to the present invention, with the ear tip shape in an unstressed condition shown in solid lines, and with the distal end of the stethoscope superimposed in dashed lines.

When the ear tip 14a is fully seated on the stethoscope ear tube, the ribs R are seated within the space between the flanges 18. Preferably, there is a slight axial clearance between the ribs R closest end 19a and the flanges 18 to facilitate proper seating of those ribs R between flanges 18. Referring now to FIG. 6, there is shown a schematic representation of what is meant when this application uses the phrase "axial clearance." The solid lines illustrate the shape of the recesses and ribs R of the ear tip in an unstressed shape (e.g. prior to when the flanges of the stethoscope are seated in the recesses). The dashed lines illustrate the flanges 18 and the end portion 16 of the stethoscope.

As illustrated, there is a slight axial clearance, in addition to a clear radial interference. The radial interference resists removal of the ear tip from the stethoscope and contributes to the desirable attachment and removal characteristics of the ear tip 14a. The axial clearance compensates for manufacturing tolerances, assists in ensuring proper seating of the ribs between the flanges 18, and affords convenient insertion of the ear tip on the end 16 of the stethoscope. With this design, most users experience a tactile indication when the ear tip is fully inserted and properly seated on the ear tubes.

Also preferably, the ear tip connection ends 16 comprise at least three flanges 18 and the channel 20a comprises at least three recesses 24a. For a length of section 16 that is less than or equal to about 0.4 inches, it has been discovered that an optimum number of flanges and ribs R for most stethoscope applications is 3 to 5; more ribs than this are not as effective, probably because the width of the ribs R have to be thinned beyond some critical level where the ribs are so thin that the ear tip rib does not properly seat.

Preferably, the ear tip engages the tubes with their flanges with a radial interference fit as described below. The maximum outer diameter (See FIG. 3) of the ear tip correction end 16 of the sound transmitting tubes between the flanges 18 should be between about 125% and 165% of the maximum inner diameter (See FIG. 6) of the channel between the molded-in recesses, and more preferably between about 135% and 155%.

Figure 7:
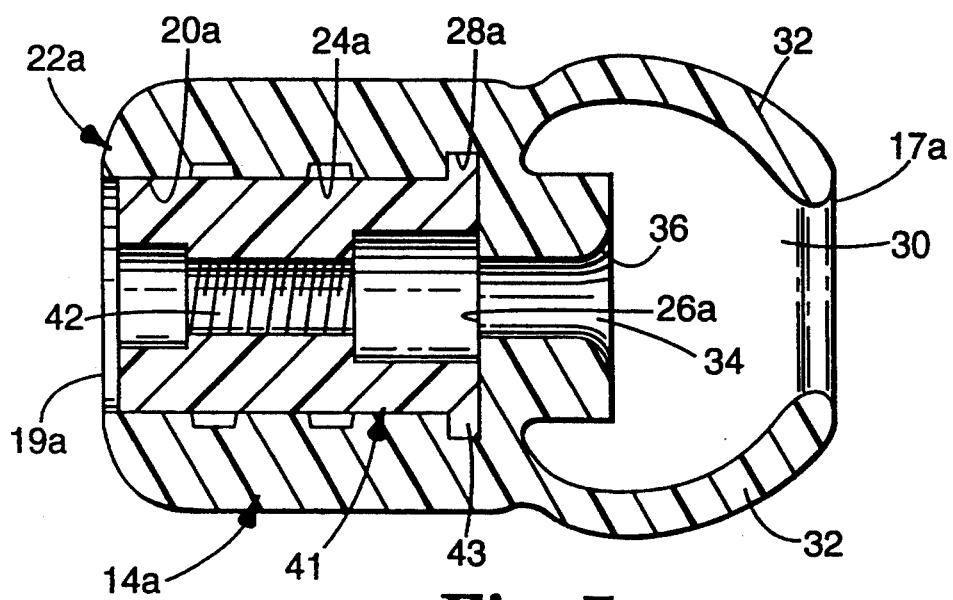
FIG. 7 is a sectional view of the ear tip of FIG. 5 shown with a threaded insert placed within the channel of the ear tip.

FIG. 7 is a sectional view of the ear tip 14a with a threaded insert 41 placed within the channel 30 of the ear tip 14a. The insert 41 has a flange 43 which is adapted to be seated in the innermost recess 28a of the ear tip 14a. The innermost recess 28a of the ear tip 14a is larger than the other recesses to accommodate the threaded insert 41. Threaded surfaces 42 of the threaded insert 41 allow the ear tip 14a to be attached to sound transmitting tubes of a stethoscope with a threaded section. Thus, the design of the ear tip 14a may be used with both a flange ended stethoscope (as shown in the present application) and a stethoscope with sound transmitting tubes with threaded ends. Of course, with the insert 41 placed within the channel 30, the ear tip 14a would not be suitable for use with the flanged ear tip engagement end of the stethoscope 10 shown in FIGS. 2 and 3. However, a suitable flanged adapter may be designed for a stethoscope with sound transmitting tubes with threaded ends to enable such a stethoscope to be directly attached to the ear tip 14a.

EXAMPLES

The following are examples of preferred embodiment of stethoscopes and ear tips according to the present invention.

EXAMPLE 1

The sound transmitting tubes 12 are preferably constructed from aluminum, with the flanges being formed by a machining process such as a turning lathe or roller from a tube having an outer diameter of about 0.23 inches. The following table illustrates dimensions for a ear tip connection end 16 according to a preferred embodiment of the present invention:

| Feature | Size Measurement (inches) |
| --- | --- |
| Ear Tip Connection End Length (e.g. 16) | 0.4 |
| Width of Flange (18) | 0.035 |
| Outer diameter of Flange 18 | 0.193 |
| Flange Spacing | 0.127 |
| Outer Diameter of Ear tip Connection End Between the Flanges 18 | 0.161 |

EXAMPLE 2

A second preferred embodiment of sound transmitting tubes is constructed from the same material and in the same manner as described above (except that the tube initially has an outer diameter of 0.182 inches) and has the following dimensions:

| Feature | Size Measurement (inches) |
| --- | --- |
| Ear Tip Connection End Length (e.g. 16) | 0.4 |
| Width of Flange (18) (e.g. W in FIG. 3) | 0.035 0.048 end flange |
| Outer diameter of Flange 18 | 0.182 |
| Flange Spacing | 0.127 |
| Outer Diameter of Ear tip Connection End 16 Between the Flanges 18 | 0.150 |

EXAMPLE 3

FIG. 5 illustrates an ear tip 14a according to the present invention with several dimensions identified by reference characters. A preferred embodiment of the ear tip 14a has the dimensions as set forth in the following table:

| Dimension | Approximate Length (inches) |
| --- | --- |
| B | 0.127 |
| C | 0.127 |
| D | 0.092 |
| E | 0.048 |
| F | 0.770 |
| X | 0.406 |
| Y | 0.103 |
| Z | 0.016 |
| R' | 0.200 |

Preferably, the ear tip is molded from a silicone elastomer such as the silicone elastomer designated as "1940-50" by Shinetsu, available locally from Gym Tech of Grape Vine, Tex. Preferably the material used to construct the ear tip has a hardness of approximately 45 Shore A. Optionally, the ear tip may be coated with a teflon like material for improved friction and antistatic properties. The teflon-like material may be applied using commercially available techniques such as the monomer gas, plasma vacuum deposition process generally available from Plasma Etch of Long Beach, Calif. The ear tip of example 3 may be used with either stethoscope identified in examples 1 and 2.

While certain embodiments of the present invention have been described in detail herein and as shown in the accompanying Drawings, it will be evident that various further modifications are possible without departing from the scope of the invention.

What is claimed is:

1. A stethoscope, comprising:
   a binaural having dual sound-transmitting eartubes adapted to deliver sound to a human ear, each having an ear tip connection end having a plurality of flanges thereon; and
   a pair of ear tips, each comprising a body formed of a non-porous elastomeric material having a channel therein and defining a longitudinal axis, said channel having a plurality of separate, individual and distinct recesses within said non-porous elastomeric material for cooperably engaging the flanges in complementary fashion such that the plurality of flanges resist longitudinal removal of the ear tip from the stethoscope.

2. A stethoscope according to claim 1 wherein the sound-transmitting eartubes have a maximum outer diameter and the flanges define a maximum flange diameter; and wherein the maximum outer diameter of the sound transmitting eartubes is greater than or equal to the maximum flange diameter.

3. A stethoscope according to claim 1 wherein each of the ear tip connection ends comprise at least three flanges, and the channel comprises at least three recesses.

4. A stethoscope according to claim 1 wherein the ear tip has an ear engagement end and an opposite end, the recesses are spaced axially along the channel, and the recess spaced farthest from said opposite end of the ear tip has a larger diameter than other recesses.

5. A stethoscope according to claim 1 wherein the ear tip connection end of each of the sound-transmitting eartubes of the stethoscope has a length of less than 0.5 inches.

6. A stethoscope according to claim 1 wherein, when the ear tip is fully inserted on the ear tip connection end, the ear tip radially interferes with the ear tip connection end of the stethoscope.

7. A stethoscope according to claim 1 wherein portions of the ear tip connection end of the sound transmitting tubes between the flanges have a predetermined maximum outer diameter, and wherein portions of the channel between the recesses have a predetermined maximum inner diameter, and further wherein said predetermined maximum outer diameter is between 135% and 155% of said predetermined maximum inner diameter.

8. An ear tip adapted for use on a stethoscope having a binaural having dual sound-transmitting eartubes adapted to deliver sound to a human ear, each eartube having an ear tip connection end having a plurality of flanges thereon, each ear tip connection end defining a longitudinal axis, said ear tip comprising:

a body formed of a non-porous elastomeric material having a channel therein having a plurality of separate, individual and distinct recesses within said non-porous elastomeric material for cooperably engaging the flanges in complementary fashion such that the plurality of flanges resist longitudinal removal of the ear tip from the stethoscope.

9. An ear tip according to claim 8 wherein each of the recesses have a diameter, and one of said recesses has a diameter that is larger than the diameter of the other recesses.

10. An ear tip according to claim 9 wherein the ear tip has an ear engagement end and an opposite end, the recesses are axially spaced along the channel and the largest diameter recess is spaced farthest from the opposite end of the ear tip.

11. An ear tip according to claim 8 wherein portions of the ear tip connection end of the sound transmitting tubes between the flanges have a predetermined maximum outer diameter, and wherein portions of the channel between the recesses have a predetermined maximum inner diameter, and further wherein said predetermined maximum outer diameter is between 135% and 155% of said predetermined maximum inner diameter.

12. An ear tip according to claim 8 wherein said ear tip is fabricated from a material selected from the group consisting of vulcanized natural rubber, vinyl elastomers, elastomeric polyurethanes, silicone rubbers, nitrile rubbers, and thermoplastic rubbers.

13. A stethoscope for delivering sound to a human ear, comprising:

a binaural having dual sound-transmitting eartubes, each having an ear tip connection end having at least three flanges thereon, said ear tip connection end having a length of less than about 0.5 inches, said sound-transmitting eartubes having a maximum outer diameter and the flanges defining a maximum flange diameter, wherein the maximum outer diameter of the sound transmitting eartubes is greater than or equal to the maximum flange diameter; and a pair of ear tips, each comprising a body formed of a non-porous elastomeric material having a channel therein and defining a longitudinal axis, said channel having at least three separate, individual and distinct recesses within said non-porous elastomeric material for cooperably engaging the at least three flanges in complementary fashion such that the plurality of flanges resist longitudinal removal of the ear tip from the stethoscope, and wherein portions of the ear tip connection end of the sound transmitting tubes between the flanges have a predetermined maximum outer diameter, and wherein portions of the channel between recesses have a predetermined maximum inner diameter, and further wherein said predetermined maximum outer diameter is between 135% and 155% of said maximum inner diameter.

14. A stethoscope according to claim 13 wherein the ear tip has an ear engagement end and an opposite end, the recesses are spaced axially along the channel, and the recess spaced farthest from said opposite end of the ear tip has a larger diameter than the other recesses.

15. A stethoscope according to claim 14 wherein the ear tip connection end of the stethoscope has a length of less than about 0.4 inches.

16. A stethoscope according to claim 15 wherein, when the ear tip is fully inserted on the ear tip connection end, the ear tip radially interferes with the ear tip connection end of the stethoscope.

17. A stethoscope according to claim 13 wherein said ear tip is fabricated from a material selected from the group consisting of vulcanized natural rubber, vinyl elastomers, elastomeric polyurethanes, silicone rubbers, nitrile rubbers, and thermoplastic rubbers.

18. A stethoscope according to claim 13 wherein the recesses are formed by at least three ribs having a base that is substantially parallel to the longitudinal axis of the ear tip, and a height measured from the base such that:

$$0.3 \, J > N > 20 \, J$$

wherein:

N = width of the base of the rib R, and
J = height of the rib R.

19. A stethoscope according to claim 13 wherein the ear tip connection end of the sound-transmitting eartubes has a longitudinal axis, the channel has a longitudinal axis and wherein each of the flanges has a width measured along that axis, and wherein the recesses have a width measured along the longitudinal axis of the channel, and further wherein
at least one flange has a width that is less than the width of its corresponding complementary recess.

20. A stethoscope according to claim 13 wherein the connection end, flanges and ear tip are constructed so that the ear tip may be repeatedly inserted on and removed from the connection end.

* * * * *